(12) United States Patent
Behling et al.

(10) Patent No.: US 10,058,292 B2
(45) Date of Patent: Aug. 28, 2018

(54) X-RAY EMITTING DEVICE WITH AN ATTENUATING ELEMENT FOR AN X-RAY IMAGING APPARATUS

(71) Applicant: KONINKLIJKE PHILIPS N.V., Eindhoven (NL)

(72) Inventors: Rolf Karl Otto Behling, Hamburg (DE); Petrus Johannes Withagen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 154 days.

(21) Appl. No.: 15/111,382

(22) PCT Filed: Jan. 6, 2015

(86) PCT No.: PCT/EP2015/050073
§ 371 (c)(1),
(2) Date: Jul. 13, 2016

(87) PCT Pub. No.: WO2015/106983
PCT Pub. Date: Jul. 23, 2015

(65) Prior Publication Data
US 2016/0338653 A1    Nov. 24, 2016

(30) Foreign Application Priority Data

Jan. 14, 2014  (EP) .................................... 14151144

(51) Int. Cl.
*A61B 6/00*    (2006.01)
(52) U.S. Cl.
CPC .................. *A61B 6/4035* (2013.01)

(58) Field of Classification Search
CPC ..................................................... A61B 6/4035
See application file for complete search history.

(56) References Cited

U.S. PATENT DOCUMENTS 6,157,703 A * 12/2000 Solomon .................. G21K 1/10
378/149

FOREIGN PATENT DOCUMENTS

| DE | 102008010224 A1 | 5/2009 |
| WO | 2008068690 A2 | 6/2008 |
| WO | 2010120525 A1 | 10/2010 |

* cited by examiner

*Primary Examiner* — Dani Fox
(74) *Attorney, Agent, or Firm* — Larry Liberchuk

(57) ABSTRACT

An X-ray emitting device (200) with an attenuating element (1) for an X-ray imaging device (100) is proposed. The attenuating element comprises a perforated sheet (3) of strongly X-ray absorbing material such as e.g. tungsten or molybdenum with a sheet thickness of e.g. less than 1 mm. The sheet (3) comprises multiple pinhole openings (5). Therein, a density of pinhole openings is higher at a center region of the sheet than at border regions of the sheet. Accordingly, a transparency to X-rays is higher at the center region than at the border regions. The pinhole openings (5) have geometries such that most parts of contours of the pinhole openings are non-parallel to edges of a focal spot (15) of an X-ray source (101) comprised in the X-ray emitting device. For example, the pinhole openings may have a circular, oval or any other cross-sectional geometry with non-linear edges. In an X-ray imaging device, such attenuating element may avoid beam hardening, needs less space than a conventional bow tie filter and is relatively insensitive to focal spot shifts.

16 Claims, 3 Drawing Sheets

X-RAY EMITTING DEVICE WITH AN ATTENUATING ELEMENT FOR AN X-RAY IMAGING APPARATUS

CROSS-REFERENCE TO PRIOR APPLICATIONS

This application is the U.S. National Phase application under 35 U.S.C. § 371 of International Application No. PCT/EP2015/050073, filed on Jan. 6, 2015, which claims the benefit of European Patent Application No. 14151144.4, filed on Jan. 14, 2014. These applications are hereby incorporated by reference herein.

FIELD OF THE INVENTION

The present invention generally relates to X-ray imaging. Particularly, embodiments of the invention relate to an X-ray emitting device with an attenuating element usable in an X-ray imaging device and to the X-ray imaging device itself.

BACKGROUND OF THE INVENTION

X-ray imaging devices are generally adapted for obtaining information about internal structures within an object of interest. For example, in medical X-ray imaging, X-ray imaging devices are used to obtain information about structures within a human body. Therein, X-rays are emitted from an X-ray emitting device comprising an X-ray source and an emitted X-ray beam is transmitted through a region of interest of the patient's body. Different types of tissues or bones within the patient's body absorb or attenuate the transmitted X-rays to different degrees. The transmitted X-rays are then detected by an X-ray detector comprising a multiplicity of detector pixels or detector elements such that from a local distribution of detected X-ray intensities information about the internal structure within the patient's body may be derived.

Generally, the X-ray source emits an X-ray beam with a relatively homogeneous X-ray intensity distribution. However, upon transmissions of the X-rays through the patient's body, some portions of the X-ray beam are attenuated more strongly than other portions. For example, portions comprising bones attenuate transmitted X-rays much more than portions with soft tissue. Accordingly, an X-ray intensity detected by the detector pixels of the X-ray detector may strongly vary throughout a detection plane of the X-ray detector. Therein, some detector pixels may starve, i.e. receive only very low X-ray intensities, such that noise may become a problem. Other detector pixels may suffer from overexposure such that these detector pixels come into overload and image quality deteriorates while at the same time the corresponding parts of the patient's body obtain an excessive X-ray dose.

Generally, in a patient's body, the more X-ray absorbing parts such as e.g. the spine are arranged centrally to a region of interest whereas in peripheral regions of the body less X-ray absorption occurs.

Accordingly, so-called bow tie filters are used to smoothen a photon flux across the X-ray detector. Such bow tie filters generally have a geometry similar to a bow tie, i.e. with a smaller thickness in the center than in the peripheral regions. Typically, a bow tie filter is made from a material with qualitatively low X-ray filtration. Ideal materials would attenuate an X-ray beam without altering its spectrum. Materials with low atomic number (Z) are preferred. The photoelectric effect, which is the dominating and highly spectral sensitive physical effect of attenuation for materials with high atomic numbers, is small for these low-Z-materials. For low-Z-materials the Compton scatter effect takes over, which is a less spectral sensitive effect of attenuation in the range of photon energies, which are relevant for human CT. For example, PTFE (Teflon®) may be used for the bow tie filter. However, as the X-ray attenuation per unit length is low, as the photoelectric effect is reduced, a bow tie filter typically needs to have a relatively large thickness of up to several cm. Accordingly, in an X-ray imaging arrangement such as in a CT (computer tomography) scanner, the bow tie filter occupies valuable space. Furthermore, beam hardening, i.e. a shift of the transmitted X-ray spectrum towards a higher average X-ray energy, cannot be completely avoided upon use of a bow tie filter, even if it is made from a low-Z-material. Both these properties may be an issue for example for helical scanning and spectral sensitive CT.

SUMMARY OF THE INVENTION

Accordingly, there may be a need for an X-ray imaging device and an X-ray emitting device for such X-ray imaging device in which an attenuating element may provide for a beneficial X-ray intensity distribution while being compact and/or spectrally neutral.

Such needs may be met by the subject-matter of the independent claims. Embodiments of the invention are defined in the dependent claims and the following specification.

According to a first aspect of the invention, an X-ray emitting device comprising an X-ray source and an attenuating element is proposed. The X-ray source is adapted for generating a focal spot from which X-rays are emitted. The attenuating element comprises a perforated sheet of strongly X-ray absorbing material with high atomic number (e.g. Z>19) and high material density. The sheet comprises a multiplicity of pinhole openings. Therein, a density of pinhole openings is higher at a center region of the sheet than at border regions of the sheet such that a transparency to X-rays is higher at the center region than at the border regions.

Preferably, the pinhole openings may have geometries such that most parts of the contours of the pinhole openings are non-parallel to edges of the focal spot. For example, the pinhole openings may have geometries in which most part of a contour of a pinhole opening is non-linear.

In order to obtain a varying density of pinhole openings in the perforated sheet, spacings between neighboring pinhole openings may be smaller at the center region than at the border regions of the sheet. Alternatively or additionally, average cross-sections of pinhole openings may be larger at the center region than at the border regions of the sheet. Overall, the pinholes may be adapted such that a transparency of X-rays at the center regions is at least twice, preferably more than ten times, as high as a transparency to X-rays at the border regions.

Preferably, the perforated sheet comprises an enlarged opening at an inner center region with full transparency, wherein the enlarged opening has a geometry in which most parts of a contour of the enlarged opening are non-linear.

The pinhole openings in the perforated sheet may have an aspect ratio of less than 1, preferably less than 0.5 or 0.2. In other words, a width or diameter of the pinhole openings is smaller than their height, i.e. smaller than a thickness of the perforated sheet. Furthermore, the pinhole openings may be adapted or configured such that a center axis of pinhole openings arranged at the center region encloses a different angle to a surface of the perforated sheet than a center axis of pinhole openings at the border regions. In other words, for example pinhole openings at the center region may be provided with their longitudinal axis being substantially perpendicular to the surface of the perforated sheet whereas in the border regions pinhole openings may be provided with their longitudinal axis being arranged non-perpendicularly with respect to the sheet surface.

In the X-ray imaging device, the pinhole openings in the attenuating element may be arranged such that lines of maximum pinhole density are non-parallel to edges of the focal spot. In other words, if for example the focal spot of the X-ray source has a rectangular shape with linear lateral edges, lines of maximum pinhole density within the perforated sheet of the attenuating element shall not be parallel to these lateral edges.

Furthermore, benefit may be taken from the fact that the attenuating element described above is mainly based on a thin sheet of X-ray absorbing material with high specific attenuation per volume and therefore requires significantly less space than conventional bow tie filters. Accordingly, in an X-ray source comprising an X-ray tube with an enclosing housing, the attenuating element may be arranged within this housing of the X-ray tube.

In one embodiment, at least a majority of the pinhole openings in the attenuating element may be arranged such as to point towards the focal spot of the X-ray source. For example, pinhole openings provided in the center region of the perforated sheet and providing for a majority of an X-ray transmission through the entire attenuating element may be arranged such as to point towards the focal spot, i.e. their longitudinal center axis crossing the focal spot. Accordingly, such pinhole openings provide for a maximum X-ray transmission. At the border regions of the perforated sheet, pinhole openings may or may not point towards the focal spot. If the pinhole openings do not point towards the focal spot, an X-ray transmission through these pinhole openings is generally reduced.

The perforated sheet of the attenuating element may be arranged in a curved geometry. For example, a flat perforated sheet may be bended. For example, a distance between the perforated sheet and the X-ray source and a curve radius of the sheet may be chosen such that the sheet focuses onto the focal spot of the X-ray source.

In an embodiment, the attenuating element comprises a stack of two or more perforated sheets of strongly X-ray absorbing material. Preferably, the X-ray emitting device further comprises an actuator for displacing individual perforated sheets within the stack relative to each other. Accordingly, by for example bending or laterally displacing the perforated sheets with respect to each other, an overall X-ray transmission through the stack of sheets may be changed.

Thus, in a preferred embodiment, a stack of perforated sheets may be arranged within a beam limiting device adjacent an X-ray source, whereby individual sheets of the stack are individually displaceable. Thus, depending on an application (scanning of an abdomen or head) or, for example, patient size, it is possible to select a specific sheet or combination of sheets that provides the optimum results for a particular application. This greatly improves the workflow in the increasingly important field of image guided therapy, in particular interventional oncology.

A second aspect of the present invention relates to an X-ray imaging device comprising the above-described X-ray emitting device according to the first aspect of the invention and further comprising an X-ray detector arranged within the X-ray beam and opposite to the X-ray source with respect to the attenuating element. The X-ray detector comprises a multiplicity of detector pixels. Therein, the attenuating element is adapted and the X-ray source, the attenuating element and the X-ray detector are arranged such that each pixel of the X-ray detector sees the focal spot through multiple pinhole openings in the perforated sheet. In other words, each X-ray detector pixel may detect portions of the X-ray beam emitted by the X-ray source, these portions being transmitted through not only one single but through a plurality of pinhole openings within the attenuating element.

Furthermore, the attenuating element may be adapted and the X-ray source, the attenuating element and the X-ray detector may be arranged such that penumbrae from different pinhole openings overlap at a detection plane of the X-ray detector.

It shall be mentioned that possible features and advantages of embodiments of the present invention are described herein partly with respect to an inventive attenuating element, partly with respect to an inventive X-ray emitting device and partly with respect to an inventive X-ray imaging device. One skilled in the art realizes that these features may be combined or replaced in suitable manners in order to come to additional embodiments of the invention.

BRIEF DESCRIPTION OF THE DRAWINGS

Embodiments of the invention will now be described with respect to the attached drawings wherein neither the description nor the drawings shall be interpreted as limiting the scope of the invention.

The figures are only schematical and not to scale. Same references indicate same or similar features throughout the figures.

DETAILED DESCRIPTION OF EMBODIMENTS

Figure 1:
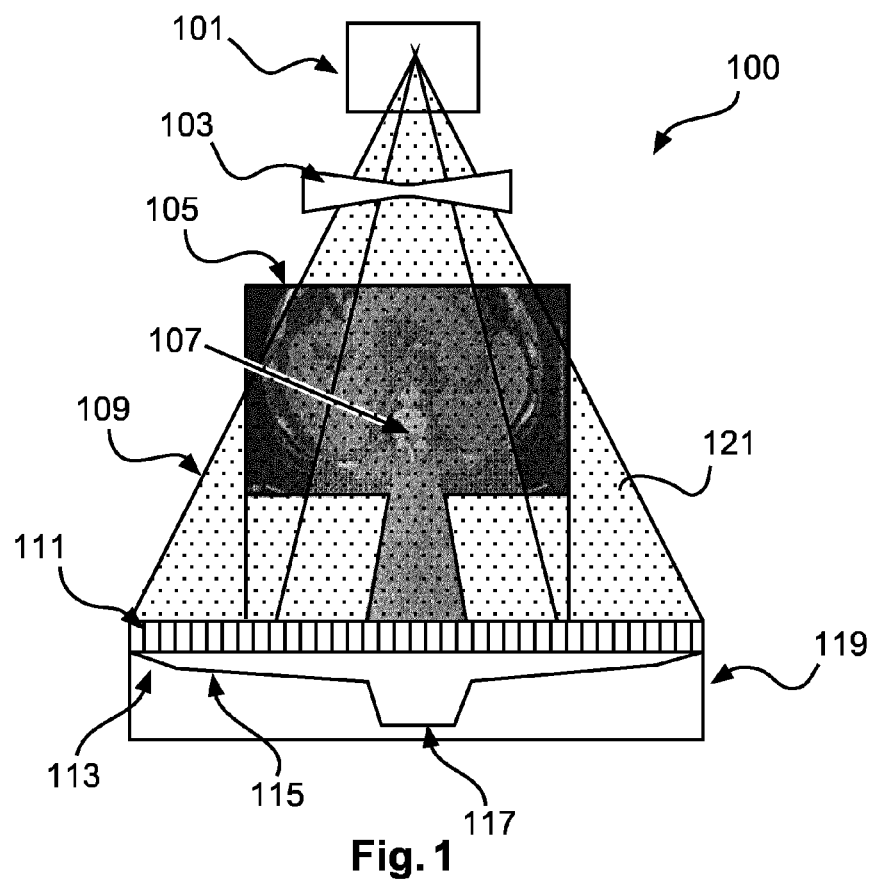
FIG. 1 shows an X-ray imaging device with a bow tie filter.

FIG. 1 shows a cross-section through an X-ray imaging device 100 with a conventional bow tie filter 103. An X-ray source 101 emits an X-ray beam 121 towards an X-ray detector 119. A patient 105 is positioned with a region of interest located within an examination volume of the X-ray imaging device 100 such that the X-ray beam 121 is transmitted through the region of interest of the patient 105. The patient comprises regions of strong X-ray attenuation such as for example bones such as the spine 107. Portions of the X-ray beam 121 transmitted through these highly attenuating portions arrive at the X-ray detector 119 with low X-ray intensity such that detector pixels 111 of the X-ray detector 119 are "starving", i.e. provide only weak signals. Such starving detector pixels 111 may suffer from noise influences. On the other hand, peripheral portions of the patient's body mainly comprise soft tissue 109 and, furthermore, these portions are X-ray-transmitted via shorter paths such that detector pixels 111 corresponding to such portions may be overexposed or over-saturated. An X-ray intensity detected by the various detector pixels 111 of the detector 119 is shown by the line 115 with a starving portion 117 at the center and over-saturated portions 113 at peripheral edges.

In order to relax the described problem of starving or over-saturated detector pixels 111, it has been proposed to interpose a filter into the X-ray beam 121. Such filter shall reduce transmitted X-ray intensity at the peripheral portions of the X-ray beam 121 while transmitting most of the X-ray intensity at a center. Accordingly, a conventional filter has been proposed to comprise a bow tie shape and is therefore referred to as bow tie filter 103. Such bow tie filter may be made from relatively weakly X-ray absorbing materials such as PTFE. At the center, the bow tie filter 103 may have a thickness of only a few millimeters whereas at peripheral portions the bow tie filter 103 may have a significant thickness of for example up to several cm. In the X-ray imaging device 100, the bow tie filter 103 is positioned upstream of the observation volume in which the patient 105 is to be arranged.

However, in many X-ray imaging devices such as CT devices there are severe space restrictions and providing a bow tie filter 103 having several cm of thickness may result in substantial space problems.

Figure 2:
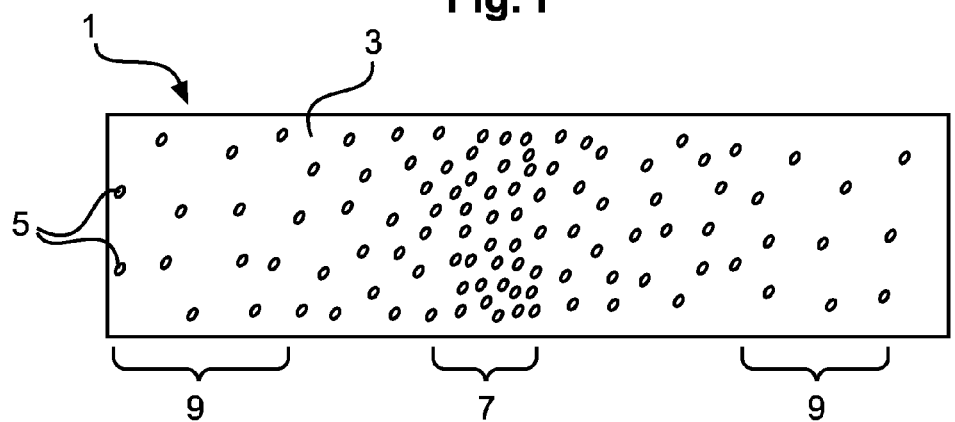
FIG. 2 shows a top view of an attenuating element for an X-ray emitting device according to an embodiment of the present invention.
Figure 3:
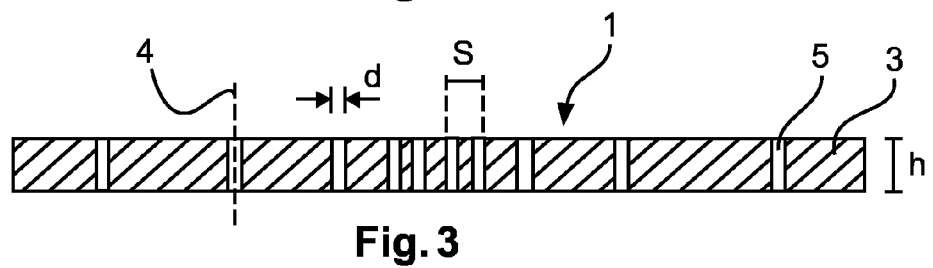
FIG. 3 shows a cross-sectional view of the attenuating element of FIG. 2.

FIGS. 2 and 3 show a top view and a cross-sectional view, respectively of an alternative attenuating element 1 for an X-ray imaging device 100 according to an embodiment of the present invention.

The attenuating element 1 comprises at least one perforated sheet 3 of strongly X-ray absorbing material. Therein, the sheet may be substantially two-dimensional, i.e. the sheet may have lateral dimensions which are substantially larger than a thickness of the sheet. For example, lateral dimensions may be in the order of several centimeters or tens of centimeters, for example between 1 and 50 cm, whereas the thickness may be in the order of a few millimeters or less, for example less than 5 mm, preferably less than 1 mm. By virtue of the low thickness of the perforated sheet 3, preferably a stack of such sheets may be provided. Thus, dependent on a current X-ray imaging application, the attenuating element 1 may comprise one or more perforated sheets, which are selected from the stack for that particular application.

The X-ray absorbing material of the perforated sheet may be chosen such that, for a given sheet thickness, substantially none, i.e. for example less than 20% or less than 10%, of an impinging X-ray intensity is transmitted through the sheet unless being transmitted through one of its pinhole openings. For example, the X-ray absorbing material may be tungsten (W) or molybdenum (Mo) or any other suitable material with preferably high atomic number of more than 19.

The perforated sheet 3 of the attenuating element 1 comprises a multiplicity of pinhole openings 5. For example, more than 100, preferably more than 1000 pinhole openings are provided. The pinhole openings may be provided in a regular pattern or irregularly, for example randomly, as shown in FIG. 2.

In the attenuating element 1, a density of pinhole openings is higher at a center region 7 of the sheet 3 than at border regions 9. Therein, the term "density of pinhole openings" may be understood as representing a fraction of accumulated cross-sectional areas of pinhole openings with respect to an overall area of the perforated sheet in a respective region 7, 9. In other words, in the center region 7, the pinhole openings may be packed more densely and/or may have a larger cross-sectional area than in the border regions 9 thereby resulting in a higher density of pinhole openings 5.

Generally, the higher the density of pinhole openings, the higher is a transparency to X-rays in a respective region 7, 9. In other words, the more pinhole openings 5 are provided in a region and/or the larger their cross-sectional area is, the higher the fraction of X-ray intensity transmitted through the attenuating element 1. For example, a transparency may vary within a range from 1 to 100%, preferably from 10% to 100%, i.e. from almost completely X-ray absorbing to completely X-ray transmitting.

For example, in the center region 7, pinhole openings 5 may be arranged such densely that an X-ray transparency of more than 20%, preferably more than 50% and even up to 100% may be achieved for the case that a larger opening is provided in the center. In other words, at or close to the center region 7, a substantial portion or even a major portion of impinging X-rays is transmitted through the attenuating element 1. Preferably, the center region 7 at an inner center region 11 may comprise an enlarged opening 13 of full transparency for completely transmitting X-ray beam portions in this inner center region 11 (see FIG. 4). The enlarged opening 13 may be substantially larger in cross-section than the pinhole openings 5, e.g. more than 50 or 200 times larger. Compared hereto, the border regions 9 or peripheral regions show a significantly lower X-ray transparency of for example less than 50%, preferably less than 20% or less than 10%.

In order to adapt the density of pinhole openings 5 and the transparency to X-rays resulting therefrom, spacings s between neighboring pinhole openings 5 and/or cross-sections of the pinhole openings may be suitably varied. For example, the cross-sections may relate to a diameter d of exemplary circular pinhole openings 5. For example, spacings s, sometimes also referred to as pitch, may be in a range between 20 µm and 1.5 mm, for example in a range between 50 µm and 1 mm. Cross-sections of pinhole openings may lie in a range from 100 µm$^2$ to 1 mm$^2$, preferably in a range from 500 µm$^2$ to 0.1 mm$^2$. In other words, the pinhole openings may have maximum lateral extensions within a range from 10 µm to 1 mm, preferably between 20 µm and 0.5 mm.

Furthermore, as the perforated sheet may have a typical thickness of between 0.2 mm and 2 mm, the pinhole openings 5 may have an aspect ratio of less than 1. This means that a height of a pinhole opening 5, which corresponds to the thickness of the perforated sheet 3 along a length of a through-hole forming the pinhole opening 5, is larger or same as a lateral dimension d of this pinhole opening 5. As explained further below, such high aspect ratio pinhole openings 5 may help in collimating or selectively transmitting portions of an X-ray beam 121.

As an example, the attenuating element 1 may be formed with a sheet of tungsten of 1 mm thickness. In such sheet 3, pinhole openings 5 with a minimum diameter of 25 µm may be formed by laser drilling. Assuming a minimum distance s of approximately 100 µm between the centers of neighboring pinhole openings 5, a maximum transparency of about 5% may be achieved when the focal spot is close to the attenuating element, e.g. less than 30 mm from the attenuating element.

As an alternative to laser drilling openings into a bulk sheet, a perforated sheet 3 for an attenuating element 1 may be fabricated by using laser-sintering processes based on tungsten powder or molybdenum powder. With such technology, minimum hole diameters of 100 µm and minimum spacings of 200 µm appear feasible, resulting in a maximum transparency of approximately 19% under the condition of the focal spot being close to the attenuating element.

Figure 4:
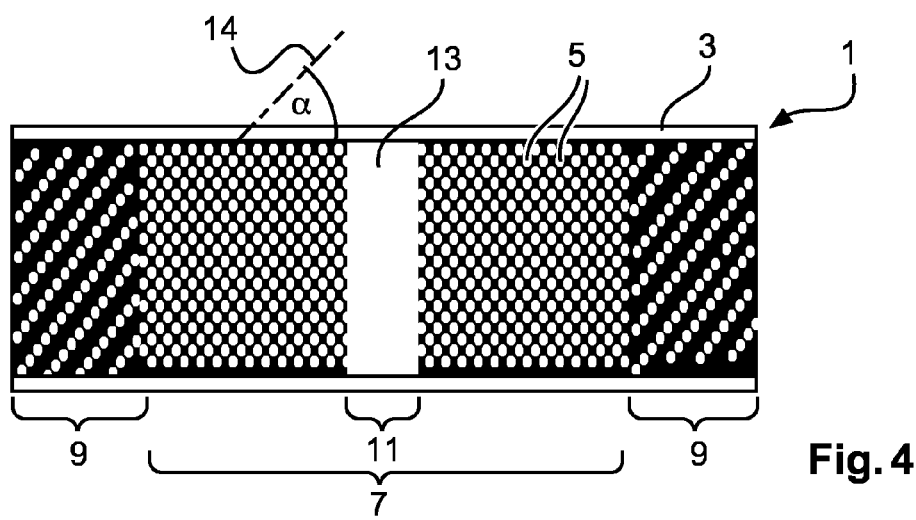
FIG. 4 shows a top view of an alternative attenuating element for an X-ray emitting device according to an embodiment of the present invention.

FIG. 4 shows a top view onto an alternative attenuating element 1. A perforated sheet 3 comprises multiple pinhole openings 5. In this case, the pinhole openings 5 are arranged in regular patterns. In a center region 7, a transparency is maximal.

At an inner center region 11, one large opening 13 is provided which extends substantially along the entire height of the perforated sheet 3, i.e. almost from an upper edge to almost a lower edge. At this inner center region 11, the attenuating element 1 has a transparency of 100%.

Adjacent to this inner center region 11, the center region 7 comprises pinhole openings 5 which are densely packed in a regular pattern. In the shown example, the pinhole openings 5 have a circular cross-section and are packed that densely such that spacings s between neighboring pinhole openings 5 are only slightly larger than diameters d of the pinhole openings 5.

In border regions 9 further away from the inner center region 11, the density of pinhole openings 5 is significantly reduced by arranging the pinhole openings 5 at another regular pattern.

In the example shown in FIG. 4, a transparency in the portions of the center region 7 adjacent to the inner center region 11 is about 25% assuming a spacing along a 45°-axis being 120 µm and a spacing along an x-axis being approximately 170 µm with a hole diameter of 80 µm. In the border regions 9, a transparency is about 4% assuming a spacing along the 45°-axis being 120 µm, a spacing along the x-axis being approximately 340 µm and a hole diameter being 80 µm.

Ideas underlying embodiments of the present invention may be understood, inter alia, as follows:

In an X-ray imaging device 100 comprising an X-ray source 101 and an X-ray detector 119, it is proposed to replace a bow tie filter 103 conventionally used for adapting an X-ray intensity distribution by a novel attenuating element 1.

The conventional bow tie filter is generally made from a weakly X-ray absorbing material. Locally varying degrees of X-ray attenuation are obtained due to a locally varying thickness of the bow tie filter material. In order to obtain sufficient X-ray attenuation at border regions of an X-ray beam 121, the bow tie filter 103 needs to be thick and is therefore space-consuming in the X-ray imaging device 100.

As a replacement for such bow tie filter 103, it is proposed to provide a thin attenuating element 1 made from a sheet 3 of strongly X-ray absorbing material. Such sheet 3 may show substantial X-ray attenuation upon a sheet thickness of e.g. less than 1 mm.

In order to obtain a locally varying X-ray attenuation, a multiplicity of pinhole openings 5, i.e. small through-holes, is provided within the sheet 3, thereby resulting in a perforated sheet. A density of pinhole openings 5 is selected to be larger at a center region 7 of the perforated sheet 3 than at border regions 9 such that transparency to X-rays is higher at the center regions 7 compared to the border regions 9 or, in other words, X-ray attenuation is stronger at the border regions 9 than at the center region 7.

In such approach, it has been found that the geometries of the pinhole openings 5 may have a significant influence. In principle, it would be possible to provide a sheet of strongly X-ray absorbing material with multiple slits included therein, each of the slits having a rectangular geometry with linear edges.

Figure 5:
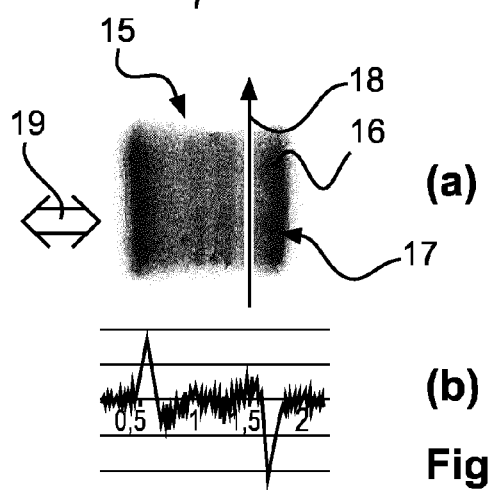
FIG. 5*a* shows a top view onto a focal spot with its X-ray emission intensity distribution.
FIG. 5*b* shows a gradient of the X-ray emission intensity distribution across line integrals of a focal spot as shown in FIG. 5*a*.

While such slits would be relatively easy to generate, it has been found that an attenuating element with such slit geometry may result in the following problems: X-ray sources or X-ray imaging devices are frequently provided such that a focal spot has a general rectangular geometry. FIG. 5(*a*) shows a distribution of emitted X-ray intensity from such rectangular focal spot 15. The arrow 18 represents a line integral in a y-direction of such intensity distribution. FIG. 5(*b*) shows a gradient across the line integrals in a x-direction. As shown in FIG. 5, the X-ray intensity of the rectangular focal spot 15 is typically highest at the borders 16 and then sharply decreases at the lateral edges 17. Therein, the lateral edges 17 have a substantial linear contour.

It has been observed that, during operation of an X-ray source, the position of the focal spot 15 may slightly vary along the x-direction as indicated by the arrow 19 in FIG. 5. In other words, during X-ray emission from the focal spot 15, the high intensity borders 16 and the sharp edges 17 are typically slightly displaced from time to time. Such lateral displacement of the focal spot 15 may cause problems, particularly when using an attenuating element with rectangular slits in which the direction of the edges of the slits coincides with the direction of the edges 17 of the focal spot 15. In such configuration, only small lateral displacements of the focal spot 15 of e.g. a few tens of micrometers may decide on whether or not a high intensity border 16 of the focal spot 15 is transmitted through one of the slits or is absorbed in the sheet material between slits. This may result in undesired instabilities during X-ray emission.

It is therefore proposed to provide an attenuating element 1 in which pinhole openings 5 are included in a perforated sheet 3, these pinhole openings 5 having geometries in which most parts of a contour of a pinhole opening 5 are preferably non-linear and non-parallel to edges of the focal spot. For example, the pinhole openings 5 may have a circular, oval or any other cross-section with non-linear edges. Having such non-linear contour in the pinhole openings 5 significantly reduces a risk of instabilities of the local X-ray flux, as measured by the detector, as the high intensity border 16 of the focal spot 15 will not be abruptly transmitted or absorbed, respectively, upon small lateral displacements 19 of the focal spot 15. Such non-linear contour of the pinhole openings 5 may be important for small pinhole openings 5 and may be even more important for larger openings such as e.g. the enlarged opening 13 forming a window at the inner center region 11 having a 100% transparency, as shown in FIG. 4. Particularly, such an enlarged opening 13 for a window should preferably not have lateral edges being linear but should have e.g. protrusions thereby resulting in a non-linear contour.

The described effect of non-linear contour and the resulting reduced risk of undesired coincidence of intensity distribution patterns in the focal spot 15 with transmission/absorption patterns in the attenuating element 1 may be further increased by providing the pinhole openings 5 in the attenuating element 1 such that lines of maximum pinhole density are non-parallel to edges 17 of the focal spot 15. This is for example indicated in FIG. 4 with a line 14 of maximum pinhole density being at an angle α of approximately 45° whereas the orientation of the edges 17 of the focal spot 15 is at about 90°. In other words, the pinhole openings 5 should be positioned such that the lines 14 of maximum pinhole density are non-orthogonal to directions, where the absolute of the gradient across sets of line integrals, as visualized in FIG. 5(b), through the focal spot intensity distribution, taken in different directions, is maximal.

Figure 8:
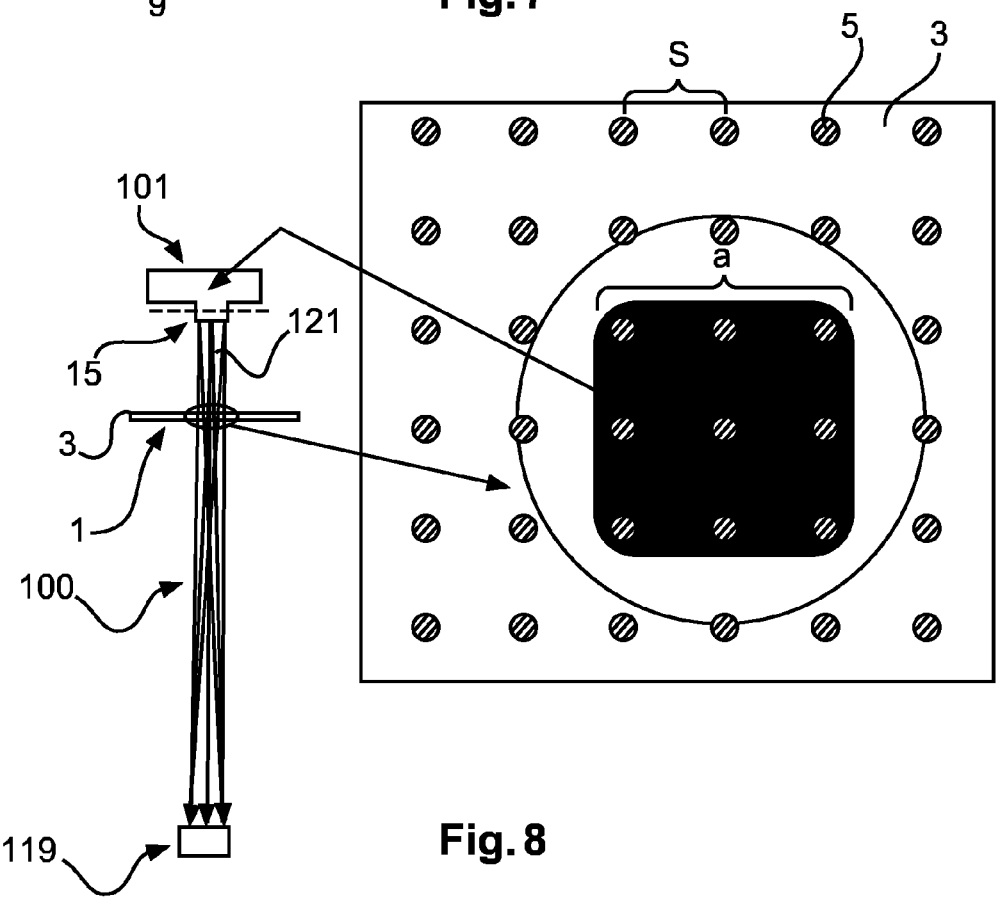
FIG. 8 shows a side view of an X-ray imaging device and an enlarged top view onto an attenuating element in such device according to an embodiment of the present invention.
Figure 9:
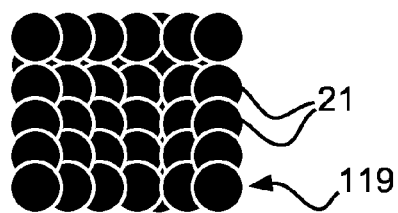
FIG. 9 shows overlapping penumbrae on a detection surface of an X-ray detector in an X-ray imaging device according to an embodiment of the present invention.

Another idea underlying embodiments of the present invention may be explained with respect to FIGS. 8 and 9. In an X-ray imaging device 100 comprising an X-ray source 101 with a focal spot 15, an X-ray detector 119 and a attenuating element 1 interposed between the X-ray source 101 and the X-ray detector 119, the attenuating element 1 should be adapted such that and the X-ray source 101, the attenuating element 1 and the X-ray detector 119 should be arranged such that each pixel 111 of the X-ray detector 119 "sees" the focal spot 15 through multiple pinhole openings 5. In other words, each detector pixel 111 should always have multiple views on the focal spot 15 as indicated on the right side top view onto the perforated sheet 3 of the attenuating element 1 in which the projection "a" of the focal spot 15 of the X-ray source 101 covers an area including nine pinhole openings 5. In such configuration, if the focal spot 15 slightly moves and therefore an X-ray intensity distribution changes locally, a residual "background" signal may remain high as other views through other pinhole openings 5 do not change or are changing less.

Preferably, when the X-ray intensity distribution locally changes due to displacements 19 of the focal spot 15 as indicated in FIG. 5, an overall X-ray flux through the attenuating element 1 towards a detector pixel may remain substantially constant as while some of the pinhole openings 5 may be transmit less to that pixel upon the X-ray intensity distribution displacement other pinholes 5 are transmitting more strongly and therefore may compensate for the changing X-ray flux towards a detector pixel.

In other words, even in areas of the attenuating element 1 with low density of pinhole openings 5, a single detector pixel 1 should always "see" the focal spot 15 through multiple pinhole openings 15. When the focal spot 15 moves and the X-ray flux to the detector 119 through the pinhole openings 5 drops, then the residual "background" signal from other views may remain high and, ideally, a compensating second view should open, i.e. a new additional pinhole opening 5 through which the detector pixel 111 sees the focal spot 15 may be available.

Preferably, the attenuating element 1 is adapted and the X-ray source 101, the attenuating element 1 and the X-ray detector 119 are arranged such that penumbrae 21 from different pinhole openings 5 overlap at a detection plane of the X-ray detector 119, as shown in FIG. 9. In other words, a position of the attenuating element 1 within an X-ray imaging device 100 and a relation of cross-sections or diameters of the pinhole openings 5 to a thickness of the perforated sheet 3 should be selected such that at the detector 119 the penumbrae 21 from different pinhole openings 5 overlap.

Figure 6:
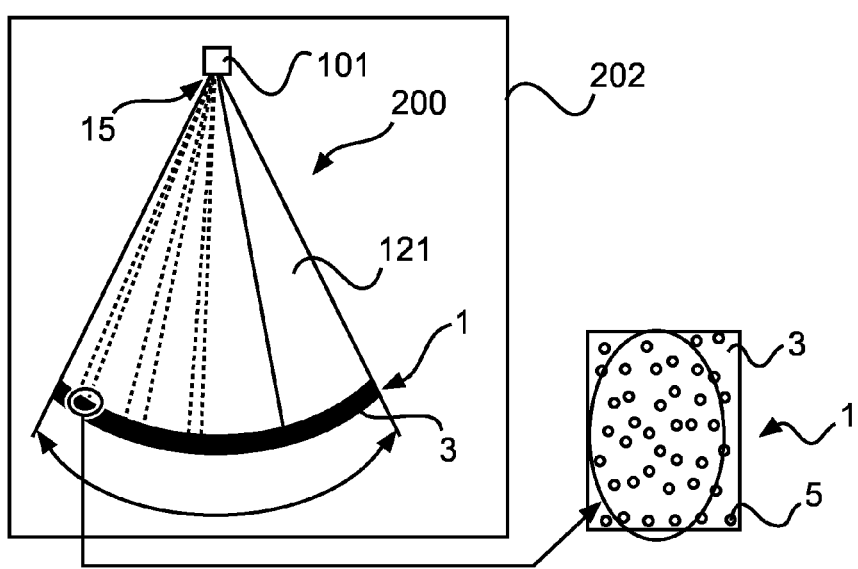
FIG. 6 shows an X-ray emission device with an attenuating element including a curved perforated sheet for an X-ray emitting device according to an embodiment of the present invention.

In an embodiment of the invention, an X-ray emitting device 200 adapted for emitting an X-ray beam 121 with a beneficial X-ray intensity distribution is proposed. Such X-ray emitting device 200 as schematically shown in FIG. 6 may comprise an X-ray source 101 having a focal spot 15 for emitting X-rays as an X-ray beam 121 and furthermore comprises a attenuating element 1 as proposed herein. The X-ray source 101 may be an X-ray tube with an enclosing housing 202 (shown in FIG. 6(a) very schematically). As the attenuating element 1 may have a very low thickness of e.g. less than 1 mm, it may be integrated into the housing of the X-ray tube.

In the exemplary embodiment shown in FIG. 6, the perforated sheet 3 of the attenuating element 1 is arranged in a curved geometry. The focus of such curved geometry may coincide with the focal spot 15 of the X-ray source 101.

Figure 7:
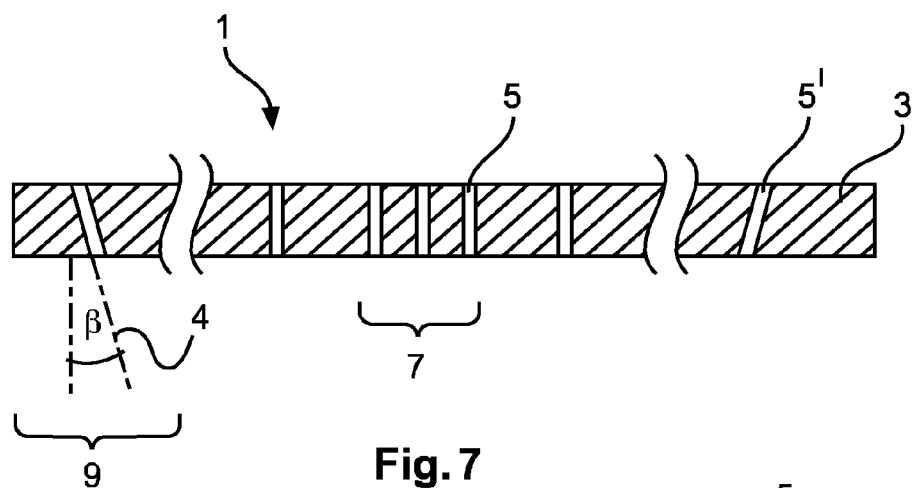
FIG. 7 shows an attenuating element with pinhole openings at locally varying angles for an X-ray emitting device according to an alternative embodiment of the present invention.

In the exemplary curved configuration shown in FIG. 6 or, alternatively, in a configuration with a planar perforated sheet 3 of an attenuating element 1, at least a majority of the pinhole openings 5 in the attenuating element 1 may be arranged such as to point towards the focal spot 15 of the X-ray source 101. The term "point towards the focal spot" may be interpreted as that a longitudinal axis 4 (as shown in FIGS. 3 and 7) of the pinhole openings 5 is directed such as to cut the focal spot 15. The term "a majority of the pinhole openings" may indicate that a number of pinhole openings 5 pointing to the focal spot 15 is larger than a number of pinhole openings 5 not pointing towards the focal spot 15. Alternatively, this term may be interpreted in that a cross-section of pinhole openings 5 pointing towards the focal spot 15 is larger than a cross-section of pinhole openings 5 not pointing towards the focal spot.

Particularly, as shown in FIG. 7, the pinhole openings 5 in the perforated sheet 3 may be provided such that in the center region 7 having the larger density of pinhole openings 5, the pinhole openings 5 are arranged rectangular to a surface of the perforated sheet 3. These central pinhole openings 5 generally point towards the focal spot 15 in an X-ray emitting device 200. At the border regions 9, pinhole openings 5 do not necessarily point towards the focal spot 15. At these border regions 9, the pinhole openings 5' may be provided in a slanted arrangement such that a center axis 4 encloses a different angle β to a surface of the perforated sheet 3 than a center axis of pinhole openings 5 at the central region 7.

By providing some of the pinhole openings 5 such as to point to the focal spot 15 and some of the pinhole openings 5', particularly in the border regions 9, such as not to point directly towards the focal spot 15, a degree of X-ray transmission through the attenuating element 1 may be suitably adapted. While for example at the center region 7 X-rays may easily pass the pinhole openings 5 as these pinhole openings are arranged such as to focus onto the focal spot 15, X-rays reaching pinhole openings 5' at the border regions 9 will not be completely transmitted through these pinholes 5' not being focused towards the focal spot 15.

In a further embodiment, two or more perforated sheets 3 may be stacked on top of each other. By displacing such stacked perforated sheets 3 with respect to each other using for example an actuator, overall X-ray transmissions through such stacked configuration may be suitably adapted.

Embodiments of the present invention may provide, inter alia, for the following benefits:

The proposed attenuating element with multiple pinhole openings may avoid beam hardening as it is conventionally observed with bow tie filters. Either X-rays pass through the pinhole openings or they are blocked. A suitable arrangement of pinhole openings such as for example a random distribution of such pinhole openings may avoid geometric correlation of structures of non-isotropic intensity in the focal spot (e.g. large flux from the line shaped edges of a double-hump focal spot, which may move orthogonal to it) and lines of symmetry of the pinhole pattern. Such characteristic may be superior for example to attenuating elements having slit apertures where the slits may be parallel to edges of a focal spot, as it may avoid large variations of a detector signal upon slight movement of the focal spot and its edges.

The thin attenuating element proposed herein may be integrated into an X-ray tube due to a much reduced space requirement compared to conventional bow tie filters. High X-ray attenuation is achievable.

An X-ray transparency through the attenuating element may be modulated during operation for example by bending the perforated sheet of the attenuating element thereby changing transmission of X-rays through the pinhole openings. Thereby, for example thermo-mechanical distortions may be compensated. An attenuation pattern may be switchable. Transparency modulation may be even increased when providing the attenuating element with a stack of multiple perforated sheets.

The perforated sheets with pinhole openings of non-linear contour may have a high mechanical stability.

LIST OF REFERENCE SIGNS 1 attenuating element
3 perforated sheet
4 central axis of pinhole opening
5 pinhole opening
7 central region
9 border region
11 inner center region
13 window of 100% transparency
14 line of maximum pinhole density
15 focal spot
16 border of focal spot
17 edge of focal spot
18 line integral through focal spot
19 displacement of focal spot
21 penumbrae
100 X-ray imaging device
101 X-ray source
103 bow tie filter
105 patient
107 spine
109 soft tissue
111 detector pixel
113 region of over-saturated pixels
115 line of X-ray intensity
117 region of starving pixels
119 X-ray detector
121 X-ray beam
200 X-ray emitting device
202 housing

The invention claimed is:

1. X-ray emitting device, comprising:
an X-ray source adapted for generating a focal spot for emitting X-rays as an X-ray beam;
an attenuating element;
wherein the attenuating element comprises:
a perforated sheet of strongly X-ray absorbing material;
wherein the sheet comprises a multiplicity of pinhole openings;
wherein a density of pinhole openings is higher at a center region of the sheet than at border regions of the sheet such that a transparency to X-rays is higher at the center region than at the border regions.

2. X-ray emitting device of claim 1, wherein the pinhole openings have geometries such that most parts of contours of the multiplicity of pinhole openings are non-parallel to edges of the focal spot.

3. X-ray emitting device of claim 1, wherein in the attenuating element the pinhole openings are arranged such that lines of maximum pinhole density are non-parallel to edges of the focal spot.

4. X-ray emitting device of claim 1, wherein the pinhole openings have geometries in which most parts of a contour of a pinhole opening are non-linear.

5. X-ray emitting device of claim 1, wherein spacings between neighboring pinhole openings are smaller and/or average cross-sections of pinhole openings are larger at the center region than at the border regions of the sheet.

6. X-ray emitting device of claim 1, wherein the perforated sheet comprises an enlarged opening at an inner center region with full transparency, and wherein the enlarged opening has a geometry in which most parts of a contour of the enlarged opening are non-parallel to edges of the focal spot.

7. X-ray emitting device of claim 1, wherein the pinhole openings are adapted such that a transparency to X-rays at the center region is at least twice a transparency at the border regions.

8. X-ray emitting device of claim 1, wherein the pinhole openings have an aspect ratio of less than 1.

9. X-ray emitting device of claim 1, wherein the pinhole openings are adapted such that a center axis of pinhole openings at the center region encloses a different angle to a surface of the perforated sheet than a center axis of pinhole openings at the border regions.

10. X-ray emitting device of claim 1, wherein the X-ray source is an X-ray tube with an enclosing housing, and wherein the attenuating element is arranged within the housing of the X-ray tube.

11. X-ray emitting device of claim 1, wherein at least a majority of the pinhole openings in the attenuating element is arranged such as to point towards the focal spot.

12. X-ray emitting device of claim 1, wherein the pinhole openings at the border regions do not point towards the focal spot.

13. X-ray emitting device of claim 12, wherein the sheet of the attenuating element is arranged in a curved geometry.

14. X-ray emitting device of claim 1, wherein the attenuating element comprises a stack of at least two perforated sheets of strongly X-ray absorbing material and wherein the X-ray emitting device further comprises an actuator for displacing individual perforated sheets of the stack relative to each other.

15. X-ray imaging device, comprising:
an X-ray emitting device according to claim 1;
an X-ray detector arranged within the X-ray beam and opposite to the X-ray source with respect to the attenuating element;

wherein the X-ray detector comprises a multiplicity of detector pixels;

wherein the attenuating element is adapted and the X-ray source, the attenuating element and the X-ray detector are arranged such that each pixel of the X-ray detector sees the focal spot through multiple pinhole openings.

16. X-ray imaging device of claim 15, wherein the attenuating element is adapted and the X-ray source, the attenuating element and the X-ray detector are arranged such that penumbrae from different pinhole openings overlap at a detection plane of the X-ray detector.

\* \* \* \* \*